United States Patent
Patil et al.

(10) Patent No.: US 12,134,590 B2
(45) Date of Patent: Nov. 5, 2024

(54) COUPLED UREA MELAMINE PRODUCTION WITH HP $CO_2$ STRIPPING

(71) Applicant: Stamicarbon B.V., Sittard (NL)

(72) Inventors: Rahul Patil, Maastricht (NL); Johannes Henricus Mennen, Meijel (NL); Lambertus Wilhelmus Gevers, Merkelbeek (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 18/688,914

(22) PCT Filed: Nov. 22, 2023

(86) PCT No.: PCT/NL2023/050614
§ 371 (c)(1),
(2) Date: Mar. 4, 2024

(87) PCT Pub. No.: WO2024/112199
PCT Pub. Date: May 30, 2024

(65) Prior Publication Data
US 2024/0270685 A1   Aug. 15, 2024

(30) Foreign Application Priority Data

Nov. 22, 2022 (EP) .................................. 22208870

(51) Int. Cl.
*C07C 273/12* (2006.01)
*B01J 3/00* (2006.01)
*B01J 3/02* (2006.01)
*C07D 251/60* (2006.01)
*C07D 251/62* (2006.01)

(52) U.S. Cl.
CPC .......... *C07C 273/12* (2013.01); *C07D 251/60* (2013.01)

(58) Field of Classification Search
CPC .. C07C 273/12; C07D 251/60; C07D 251/62; B01J 3/00; B01J 3/02
See application file for complete search history.

(56) References Cited

U.S. PATENT DOCUMENTS

| | | |
|---|---|---|
| 2004/0162429 A1 | 8/2004 | Noe et al. |
| 2016/0318883 A1 | 11/2016 | Mennen |
| 2020/0385339 A1 | 12/2020 | Patil et al. |
| 2021/0060519 A1 | 3/2021 | Scotto et al. |

FOREIGN PATENT DOCUMENTS

| | | |
|---|---|---|
| EP | 2385043 | 11/2011 |
| WO | 98/08808 | 3/1998 |

OTHER PUBLICATIONS

International Search Report and Written Opinion in PCT Application No. PCT/NL2023/050614, mailed Feb. 22, 2024 (9 pages).
"Urea-melamine plant integration", Nitrogen + Syngas 321, Jan.-Feb. 2013, p. 44-54,.
Ullmann's Encyclopedia of Industrial Chemistry, vol. 21, chapter Melamine and Guanamines, 2003.
Ullmann's Encyclopaedia, chapter Urea, 2010.

*Primary Examiner* — Bruck Kifle
(74) *Attorney, Agent, or Firm* — Leason Ellis LLP

(57) ABSTRACT

The disclosure pertains to a coupled plant process for the production of urea and melamine, with a urea synthesis section with HP $CO_2$ stripping, and with a part of the $CO_2$ feed supplied to a recovery section.

20 Claims, 1 Drawing Sheet

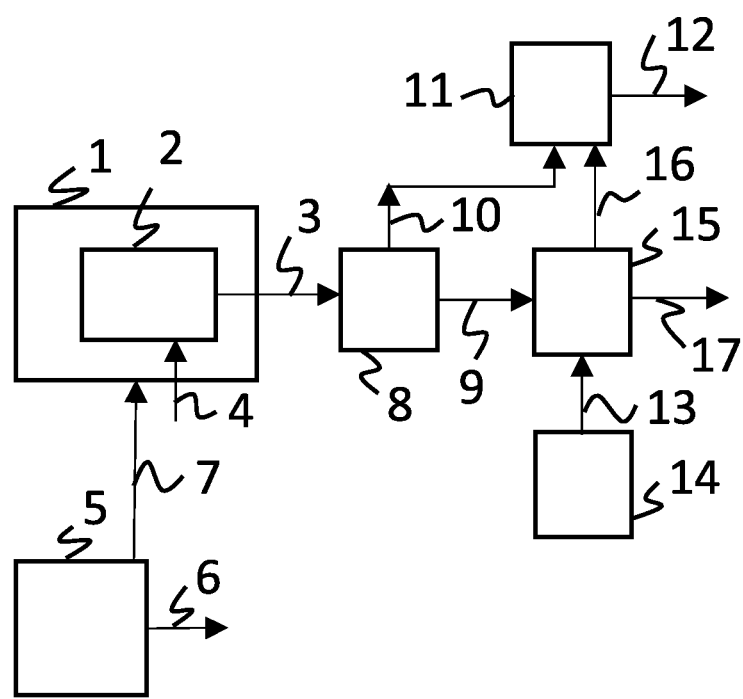

COUPLED UREA MELAMINE PRODUCTION WITH HP $CO_2$ STRIPPING

CROSS-REFERENCE TO RELATED PATENT APPLICATIONS

Field

This application is a U.S. National Stage Application under 35 U.S.C. § 371 of International Patent Application No. PCT/NL2023/050614, filed Nov. 22, 2023, which claims the benefit of priority of European Patent Application No. 22208870.0, filed Nov. 22, 2022, both of which are incorporated by reference in their entireties.

The invention pertains to the coupled production of urea and melamine.

Introduction

Various types of urea production processes are described in Ullmann's Encyclopedia, chapter Urea, 2010.

The article "Urea-melamine plant integration", Nitrogen+Syngas 321, January-February 2013, p.44-54, describes various approaches to urea-melamine integration.

There remains a desire for the improved coupling of a relatively large melamine production plant to a urea production process with a HP urea synthesis section of the $CO_2$ stripping type, in particular with a relatively large amount of off-gas from the melamine plant recycled to the HP urea synthesis section, relative to the urea production in the HP urea synthesis section. Particularly desired are high energy efficiency and low equipment costs. The coupled plant and process comprise a urea production section with a urea synthesis section, recovery section, and waste water treatment (WWT) section. The WWT comprises e.g. a hydrolyser and a desorber and is energy-consuming (relatively high steam consumption per kg water treated). The WWT section typically also comprises a reflux condenser.

SUMMARY

The invention pertains in a first aspect to a coupled process for the production of urea and melamine, the process comprising: producing urea in a high pressure urea synthesis section comprising a high pressure (HP) $CO_2$ stripper yielding a stripped urea solution, wherein the HP $CO_2$ stripper uses a first part of a gaseous $CO_2$ feed stream as stripping agent; producing melamine in a melamine production section thereby also releasing melamine off-gas; supplying said melamine off-gas, optionally as condensate, directly or indirectly to the high pressure urea synthesis section; supplying the stripped urea solution directly or indirectly via a liquid flow connection to a low pressure (LP) dissociator, yielding purified urea solution and a low pressure gas stream; subjecting the low pressure gas stream to condensation in a low pressure (LP) carbamate condensation zone with a second part of the gaseous $CO_2$ feed stream to form a carbamate solution.

The invention also pertains to a coupled plant for the production of urea and melamine, the plant comprising: a high pressure urea synthesis section for producing urea, comprising a high pressure (HP) $CO_2$ stripper having an outlet for a stripped urea solution, and an inlet for a first part of a gaseous $CO_2$ feed stream used as stripping agent; a melamine production section having an outlet for melamine and an outlet for melamine off-gas; a fluid flow connection for supplying said melamine off-gas, optionally as condensate, directly or indirectly to the high pressure urea synthesis section; a liquid flow connection for supplying the stripped urea solution directly or indirectly to a low pressure (LP) dissociator having an outlet for a purified urea solution and an outlet for a low pressure gas stream; a low pressure (LP) carbamate condensation zone configured for subjecting the low pressure gas stream to condensation with a second part of the gaseous $CO_2$ feed stream to form a carbamate solution, the plant comprising a gas flow connection from a $CO_2$ supply unit to the LP carbamate condensation zone.

Hence, the invention pertains to a coupled process and plant for the production of urea and melamine, with urea synthesis with HP $CO_2$ stripping, and with a part of the $CO_2$ feed supplied to an LP recovery section.

BRIEF DESCRIPTION OF THE DRAWINGS

FIG. 1 schematically illustrates an example process scheme according to the invention. Any embodiments illustrated in the FIGURE(s) are examples only and do not limit the invention.

DETAILED DESCRIPTION

The inventive process and plant enable the coupling of a relatively large melamine production process to a urea production process with a HP urea synthesis section of the $CO_2$ stripping type; i.e. in terms of a relatively high amount of melamine off-gas recycle to the urea synthesis section compared to the urea production rate and compared to fresh $NH_3$ feed and $CO_2$ feed, and in particular without upset of downstream sections such as an LP recovery section and/or without significant increase of the duty of the wastewater treatment section. Moreover, the inventive process and plant avoid the need for costly equipment such as a dedicated $NH_3$ condenser and permits for relatively smaller size condensers in the LP section, and in preferred embodiments also for the WWT.

Very elegantly, the inventive plant and process mitigate the relative lack of $CO_2$ feed available for stripping in the HP urea synthesis section in case of a relatively large amount of melamine off-gas recycled to the synthesis section.

An advantage of the invention is that the steam consumption of the HP stripper can be relatively low.

Ullmann's Encyclopaedia, chapter Urea, 2010 mentions that in a urea process of the (Stamicarbon) $CO_2$ stripping type, i.e. without integration with a melamine plant, only one low pressure recirculation stage is required due to the low ammonia and carbon dioxide concentrations in the stripped urea solution. The present invention, on the other hand, permits a relatively high N/C ratio of the stripped urea solution.

Aspects of the invention will now be further illustrated, using for convenience references to FIG. 1, which FIGURE illustrates an example process and plant according to the invention and does not limit the invention or the claims.

The invention provides a coupled process and plant for the production of urea and melamine. The process and plant are coupled in that off-gas from the melamine production is supplied to the urea production. Optionally, the process is also integrated in that urea melt is supplied from the urea production to the melamine productions section.

The plant generally comprises a urea production section comprising a high pressure urea synthesis section (1) and a recovery section, and typically a WWT and typically an evaporation section.

The process comprises producing urea in a high pressure urea synthesis section (1) comprising a high pressure (HP) $CO_2$ stripper (2) yielding a stripped urea solution (3). The HP $CO_2$ stripper (2) uses a first part (4) of a gaseous $CO_2$ feed stream as stripping agent, in particular as high pressure gaseous $CO_2$ stream. $CO_2$ stripping is used to create a low partial vapor pressure of $NH_3$ in the stripper tubes to promote the decomposition of carbamate in the urea solution, further using heating. The gaseous stream for $CO_2$ stripping comprises at least 90 vol. % $CO_2$, typically at least 95 vol. % $CO_2$, balance inerts, typically including some air used for passivation. The stripper is typically a shell-and-tube heat exchanger configured for counter-current contact in the tubes of a falling film of urea solution to be stripped with the gaseous stripping agent. The stripper typically has a liquid inlet for urea solution at the top, a liquid outlet for stripped urea solution at the bottom, an inlet for $CO_2$ gas used as strip gas at the bottom, and an outlet for a gas stream at the top, all at the tube side. Heating fluid such as steam is present on the shell side.

The synthesis section further comprises a reaction zone and a condensation zone. These zones may be provided as separate units, such as a urea reactor and a high pressure carbamate condenser, or combined in a single vessel, such as a pool reactor. Optionally, two or more condensation zones are used, for instance in parallel or in series. Optionally, two or more reaction zones are used, for instance in parallel or in series.

A urea reactor is typically a vertical urea reactor with one or more inlets at the bottom and one or more outlets for withdrawing urea synthesis solution from an upper part of the reactor. The urea synthesis solution comprises urea, water, carbamate, and $NH_3$. The HP stripper is used for stripping urea synthesis solution to cause dissociation and removal of a part of the carbamate.

The HP carbamate condenser is typically a shell-and-tube heat exchanger, preferably but not exclusively with gas to be condensed in the shell side space and cooling liquid in the tube bundle. The HP carbamate condenser has an outlet for a HP carbamate stream to the urea reactor; the gas outlet of the stripper is connected to the HP carbamate condenser. In embodiments with condensation of gas from the stripper on the shell-side space of the HP carbamate condenser, already some urea can be formed in the HP carbamate condenser.

In embodiments with a pool reactor, a horizontal vessel is provided comprising a condensation zone and a reaction zone; having an inlet for gas from the stripper to the condensation zone and an outlet for urea synthesis solution from the reaction zone to the stripper. The condensation zone of the pool reactor is provided by the part of the vessel where a U-shaped tube bundle for cooling liquid, and is in fluid connection (for gas and liquid) with the reaction zone which is provided between the bend of the tube bundle and the vessel wall. Typically, the pool reactor comprises a separate gas outlet and liquid outlet provided at the reaction zone. Advantageously, the pool reactor comprises a sparger (gas distributor) for gas from the HP stripper extending through both the condensation zone and the reaction zone. Optionally, a pool reactor is combined with a downstream urea reactor, e.g. vertical urea reactor, arranged between the reaction zone of the pool reactor and the HP stripper. Optionally, the pool reactor or HP carbamate condenser comprises two tube bundles for two different cooling liquids.

In a preferred embodiment, the reaction zone is operated with a synthesis pressure of 130-150 bara. In a further embodiment, the reaction zone, condensation zone, and HP stripper are all operated at a pressure in the range 130-150 bara.

In a preferred embodiment, the reaction zone is operated with an N/C ratio of 3.0-3.2. The relatively low N/C ratio in the reaction zone is advantageous in enabling carbamate recycle from downstream sections, in particular to enable the recycle from the recovery sections to be exclusively as carbamate solutions.

The process comprises supplying the stripped urea solution (3) directly or indirectly via a liquid flow connection to a low pressure (LP) dissociator (8). The treatment, in particular heating, in the LP dissociator yields a purified urea solution (9) and a low pressure gas stream (10). The LP dissociator comprises for instance a shell-and-tube heat exchanger, used for decomposing carbamate from the stripped urea solution. The LP gas stream comprises $CO_2$ and $NH_3$.

In an example embodiment, the purified urea solution is expanded, e.g. to atmospheric pressure, and preferably flashed with gas/liquid separation. Preferably the resulting gas is condensed in a condenser, e.g. in an atmospheric condenser, and the liquid, i.e. urea solution, is supplied to a heating unit, preferably a pre-evaporator operating at sub-atmospheric pressure of e.g. 0.2 bara to 0.5 bara; with gas-liquid separation of the resulting heated urea solution. Urea solution from the pre-evaporator is supplied, e.g. via a urea solution storage tank, to e.g. to a vacuum evaporation section and the resulting urea melt is supplied e.g. in part to the melamine production section and e.g. in part to a urea finishing section for solidification into a solid urea product.

A relatively low free N/C ratio of the urea the urea solution at the inlet of the atmospheric flash is advantageous for the operation of the atmospheric condenser, and for the condensation of gas obtained from the urea solution downstream of the atmospheric flash.

The process involves subjecting the low pressure gas stream to condensation in a low pressure (LP) carbamate condensation zone (11) to form a carbamate solution (12). The LP carbamate condensation zone is provided e.g. as a single condensation unit, or as two or more condensation units in series and/or in parallel, for example using a first and a second LP carbamate condensation units in series.

For instance, in a possible embodiment, a first gas stream is condensed in a first condenser, which also receives an aqueous stream, and the resulting carbamate solution is supplied to a second condenser receiving a second gas stream to give a second carbamate solution.

For all configurations of the LP carbamate condensation zone, the carbamate solution is recycled to the HP urea synthesis section, optionally through, e.g., an MP carbamate condenser. The plant hence comprises an LP recovery section comprising the LP dissociator and the LP carbamate condensation zone. Optionally, the condensation in the first LP carbamate condensation unit is partial, e.g. in the range of 10-60% of total $CO_2$ supplied to the condenser, and gas from the first LP carbamate condensation unit, comprising $NH_3$ and $CO_2$, is subjected to further condensation in the second LP carbamate condensation unit. The first and second carbamate condensation unit may be operated with different cooling liquids. The temperature at the carbamate outlet (e.g. shell side) of the first carbamate condensation unit is e.g. in the range 80-100° C.; and for the second carbamate condensation unit e.g. below 75° C., e.g. in the range 50-75° C.; for instance the carbamate outlet temperature of the second unit is at least 10° C. lower than for the first unit. The second LP carbamate condensation unit preferably uses cooling water and has a preferred minimum carbamate outlet temperature of 50° C.

The LP carbamate condensation zone, in particular the first carbamate condensation unit, preferably also receives an aqueous liquid stream, e.g. clean process condensate or lean carbamate solution from a wastewater treatment section (WWT) of the urea plant, or for instance condensate from the atmospheric condenser.

Preferably, the condensation in said LP carbamate condensation zone (11) is, at least in part, conducted in indirect heat exchange with a urea solution to be heated, in particular with urea solution in a pre-evaporator. Preferably the condensation in the first LP carbamate condensation unit is in indirect heat exchange with urea solution to be heated.

The heated urea solution is e.g. at a pressure of 0.5 bara or less, e.g. in 0.2-0.5 bara. Accordingly, the first LP carbamate condensation unit is preferably provided on the shell side of a shell-and-tube heat exchanger with urea solution to be heated in the tubes, the tube side providing a pre-evaporator of the urea plant. Preferably, this first LP carbamate condensation unit receives a part of the $CO_2$ feed as a gaseous stream.

Preferably, the amount of $CO_2$ and $NH_3$ condensed into carbamate in the first LP carbamate condensation unit, which is in indirect heat exchange with urea solution to be heated, is at least 80% or at least 100% of the amount of $CO_2$ and $NH_3$ condensed into carbamate in a downstream second carbamate condensation unit, which uses e.g. cooling water.

In the inventive process, a second part (13) of the gaseous $CO_2$ feed stream is also subjected to condensation in the LP carbamate condensation zone (11), for example in the preferably used first LP carbamate condensation unit. In particular the second part of the gaseous $CO_2$ feed stream is introduced into the carbamate condenser as a gaseous stream having an N/C ratio of lower than 2.0, preferably lower than 1.8. Thereby the N/C ratio of the formed carbamate solution (12) is advantageously decreased, permitting to achieve a high degree of condensation of the gases supplied to the LP carbamate condensation zone as LP carbamate solution. Thereby transport of $NH_3$ to downstream sections is avoided, which reduces the duty of the WWT.

A lower N/C ratio of LP carbamate condensation zone also contributes to an advantageous higher condensation temperature, permitting lower water recycle to the urea synthesis section and increasing urea conversion. Moreover, with the preferred heat integration, in particular by the pre-evaporator, the heat of condensation of the part of the $CO_2$ feed stream is advantageously at least in part recovered and used for heating urea solution.

The carbamate solution obtained from the LP carbamate condensation zone for instance has an N/C ratio of 2.0-3.2, based on composition at the final liquid stream.

The LP carbamate condensation zone is for instance operated with a pressure of at least 3.0 bara, at least 4.0, at least 4.5, at least 5.0, or at least 5.5 bara, and generally up to 10 bara, based on outlet pressure. Preferably the LP carbamate condensation zone receives the second part (13) of the gaseous $CO_2$ feed stream as a gas stream at said pressures. The LP carbamate condensation zone is preferably connected to an LP dissociator operating at the same pressure; and receives both gas from the LP dissociator and the second part (13) of the gaseous $CO_2$ feed stream as gas streams, and in an example embodiment said gas streams are combined to form a combined gas stream that is supplied to the LP carbamate condensation zone.

Preferably, the second part (13) of the gaseous $CO_2$ feed stream is for example at least 2 mol. %, or at least 5 mol. %, or at least 10 mol. %, and/or for instance less than 25 mol. %, or less than 20 mol. %, or less than 15 mol. %, optionally in the range of 2-20 mol %, or 2-10 mol. %, or 10-20 mol. %, of the total $CO_2$ feed stream, on the basis of $CO_2$. In embodiments with the contacting unit, e.g. LP stripper, these values may refer in particular to the gas inlet of said unit. Preferably the amount of $CO_2$ in the gas stream at the gas outlet of the contacting unit (e.g. LP stripper) is also in these ranges, and preferably the gas at this outlet is supplied directly to a gas inlet of the LP condensation zone. In this way, the heat of condensation of the $CO_2$ comprised in the gas at the gas outlet of the contacting unit is preferably recovered by heat integration with the preferred pre-evaporator.

For instance 10-50% of the $CO_2$ supplied to the LP counter-current contacting unit (in particular, stripper) is absorbed in the liquid in said unit, and the remaining part, e.g. at least 50% of the $CO_2$ received at the gas inlet, exits the unit (LP stripper) through the gas outlet and is supplied to the LP condensation zone.

Typically, the gaseous $CO_2$ feed stream is obtained from battery limit, and is preferably supplied at least in part in uncondensed, gaseous form, to an inlet of the LP carbamate condensation zone. For instance the gaseous $CO_2$ feed stream is made available at a pressure of max. 10 bara at the battery limit.

In a further possible embodiment, a further part of the $CO_2$ feed is supplied to another unit of the urea production plant, such as to a vertical urea reactor.

In a preferred embodiment, the purified urea solution (9) is brought in counter-current contact (15) in a contacting unit with the second part (13) of the gaseous $CO_2$ feed stream, in particular at LP, preferably at a pressure of at least 3.0 bara, at least 4.0, at least 4.5, at least 5.0, or at least 5.5 bara, and generally up to 10 bara. Preferably this contacting is performed at substantially the same pressure as the LP dissociation, e.g. max. 0.10 bar lower than the dissociation. Accordingly, it is not preferred to perform flashing between the dissociation and the counter-current contacting.

The counter-current contacting is preferably performed at a temperature of the urea solution at the inlet of at least 120°, e.g. 120° C.-150° C.

Thereby advantageously the N/C ratio of the purified urea solution is reduced, and advantageously at least some of the $NH_3$ is removed from the urea solution. This advantageously reduces the slip of $NH_3$ to downstream sections and can reduce the duty on the WWT.

The contacting step yields a liquid stream (17) (the urea solution) and a gaseous stream (16), and the gaseous stream is supplied to the LP carbamate condensation zone (11). The gaseous stream is, in this embodiment, supplied from the contacting unit (15) to the LP carbamate condensation zone (11) through gas flow line (16).

This contacting step may in particular be advantageous in embodiments wherein the purified urea solution is, after the counter-current contact, expanded to a lower pressure, e.g. atmospheric pressure, preferably with gas/liquid separation (e.g. atmospheric flash). Preferably the resulting gaseous stream is condensed, in one or more units such as a condenser or an absorber, with the resulting condensate supplied, directly or indirectly via a liquid flow connection, to a waste water treatment section. The waste water treatment (WWT) section, as typically comprised in the urea production section, comprises e.g. a hydrolyser and a desorber and is energy-consuming (relatively high steam consumption per kg water treated). The WWT section typically also comprises a reflux condenser. The contacting step advantageously reduces the duty of the WWT and increases energy efficiency.

The counter-current contacting is preferably adiabatic.

In a preferred embodiment, the second part (13) of the gaseous $CO_2$ feed stream is used, at least in part, for low pressure stripping of the purified urea solution (9), wherein the stripping is preferably adiabatic, to enable said counter-current contacting.

Preferably, the process comprises medium pressure treatment of the stripped urea solution upstream of the LP dissociator, i.e. between the HP stripper and the LP dissociator. In an embodiment, the MP treatment comprises, or consists of, adiabatic flashing. In an embodiment, the MP treatment comprises heating the urea solution at medium pressure and subsequent gas/liquid separation; preferably with preceding flashing at medium pressure. Flashing involves expansion of the urea solution and gas/liquid separation, e.g. in a flash unit having a gas outlet and a separate liquid outlet. The MP heating is for instance conducted in a heat exchanger using steam as heating fluid, or for example by supplying the MP urea solution, after expansion to MP and gas/liquid separation, to a tube bundle of a HP carbamate condenser with condensation of gas from the HP stripper in the shell, to heat the MP urea solution. Generally, the use of MP treatment advantageously reduces the total carbamate load on the LP section and thereby can increase urea conversion.

The MP treatment yields an MP gas stream, comprising $CO_2$ and $NH_3$, and is supplied to an MP carbamate condensation section (which can also be an absorber), typically also receiving carbamate solution from the LP carbamate condensation zone, to form MP carbamate solution, which is recycled to the HP urea synthesis section. The MP carbamate condenser may be provided by one or more condensation units in series and/or in parallel. A gas stream comprising inert components from the urea synthesis section can also be condensed in the MP carbamate condensation section. Thereby advantageously a scrubber in the HP urea synthesis section may be dispensed with.

The process comprises producing melamine (6) in a melamine production section (5) thereby also releasing melamine off-gas (7). The type of melamine production section is not particularly limited. Both high pressure (>70 bar abs.) melamine processes and low pressure processes (<70 bar abs.) can be used, high pressure melamine processes are preferred, in particular high pressure non-catalytic liquid phase melamine synthesis. Various suitable melamine production processes are described in Ullmann's Encyclopedia of Industrial Chemistry, volume 21, chapter Melamine and Guanamines, 2003. Further examples of suitable melamine production processes are described in US20040162429A1, EP2385043A1 and EP3597641. However, other types of melamine production processes can also be used. The melamine off-gas comprises $NH_3$ and $CO_2$ and, possibly, water. In some embodiments, the melamine production section comprise two melamine production trains in parallel.

At least a part, preferably all, of the melamine off-gas (7) is supplied directly or indirectly to a urea reaction zone, preferably to the urea production process, in particular preferably to the high pressure urea synthesis section (1), optionally as condensate. The off-gas is for instance introduced in gaseous form in the urea synthesis section, or as condensate (carbamate solution). The off-gas is for instance introduced in gaseous form in the urea synthesis section and condensed in a carbamate condenser comprised in said section. The off-gas is for instance in a melamine off-gas condenser and the resulting condensate is supplied to the urea synthesis section.

In yet a further embodiment, the melamine off-gas is supplied to a dedicated urea reaction zone. For instance, the melamine off-gas is condensed in a melamine off-gas condenser and the resulting condensate is supplied to a dedicated urea reactor. Or, for instance, the melamine off-gas is condensed in a melamine off-gas condenser also including a reaction zone, e.g. a pool reactor or pool condenser. The urea reactor may be a part of a dedicated or tied-in urea plant, e.g. as described in US20210060519.

In yet a further embodiment, the off-gas is condensed in a melamine off-gas condenser operating at a pressure off, e.g., at least 80 bar, and the resulting carbamate solution is supplied to a dedicated urea reaction zone, i.e. a reaction zone additional to and distinct from the urea reaction zone of the urea synthesis section, which zone can be a separate vessel (e.g. a urea pre-reactor) or a part of the melamine off-gas condenser, e.g. in case of a pool condenser, such that a part of the carbamate is converted into urea. The resulting urea-containing solution is supplied to the urea synthesis section, wherein said urea-containing solution typically comprises carbamate.

In case of condensation, a dedicated off-gas condenser can be used, part of the melamine plant, urea plant, or in between, of combined condensation can be used, for instance in a MP recovery section of the urea plant. Combinations are also possible. Indirect recycle in particular refers to recycle through a condensation section, for example a condensation section of the urea production plant, for instance a condensation section of an MP recovery section. Some example configurations for the supply of the off-gas to the urea plant are described in US20160318883A1.

The manner of recycle of the off-gas to the HP urea synthesis section is not particularly limited.

In embodiments wherein the off-gas is supplied as condensate, the off-gas is condensed into carbamate solution, for instance between 20 and 110 bar, and supplied for example to the HP carbamate condenser. In embodiments wherein the melamine synthesis section operates at a pressure above the pressure of the HP carbamate condenser, the melamine off-gas is, for example, introduced in the urea synthesis section in gaseous form.

The inventive process and plant are especially advantageous at relatively large amounts of melamine off-gas relative to urea production.

Preferably, the amount of the melamine off-gas stream supplied to the HP urea synthesis section corresponds to the conversion into melamine of an amount of urea of at least 5%, at least 10%, or at least 20%, or at least 30%, and/or up to 50% of the total urea produced in the high pressure urea synthesis section, preferably 10 to 45 wt. %; all amounts suitably as mass flow rates.

Preferably, the amount of $CO_2$ in the melamine off-gas stream supplied to the HP urea synthesis section is at least 5%, or at least 10%, or at least 15%, and/or up to 25% of the amount of $CO_2$ converted into urea in the HP urea synthesis section; all amounts as kg/hour. The remaining part of the $CO_2$ is provided as gaseous $CO_2$ feed.

For example, the urea production in the synthesis section is 100 ton/hr and the amount of melamine off-gas corresponds to a urea melt feed of 15 ton/hr to the melamine production section. In some embodiments, at least 10 wt. %, or at least 20 wt. % or at least 30 wt. % and/or up to 50 wt. % of the urea produced in the urea synthesis section is supplied to the melamine synthesis. In some embodiments, the melamine synthesis also receives urea from additional urea plants. In some embodiments, the amount of off-gas originates from two or more melamine plants.

A problem when the amount of recycled melamine off-gas is relatively large compared to the urea production rate, is that the efficacy of the HP stripper (stripping efficiency α) decreases, whereas steam consumption and required steam pressure of the HP stripper increase, due to amount of fresh $CO_2$ feed to the synthesis section, that can also be used for stripping, being smaller compared to the amount of urea synthesis solution to be stripped. Thereby the N/C ratio of the stripped urea solution (calculated on the basis of free $NH_3$, $CO_2$ and carbamate, disregarding urea) increases, to for instance 2.3 or higher, for example in the range 2.4 to 3.0. The present process advantageously mitigates this effect by supplying a second part of the fresh $CO_2$ feed to the LP carbamate condensation zone. Accordingly, the process involves decreasing the N/C ratio in the LP carbamate condensation section.

It is noted that in the present invention, it is advantageously not necessary to operate the HP stripper with a very high energy consumption to achieve a sufficiently low N/C ratio of the stripped urea solution and a sufficiently low N/C ratio in the LP carbamate condensation section.

Advantageously, preferred embodiments of the process do not involve the recycle of a stream of condensed $NH_3$ from a recovery section, i.e. a section comprising a unit for treating urea solution originating from the HP $CO_2$ stripper to recover $NH_3$ and $CO_2$, to the HP urea synthesis section, as an additional stream to the recycle stream of carbamate solution. Preferred embodiments of the plant do not comprise an $NH_3$ condenser having a fluid flow connection to the HP synthesis section that is separate from and additional to the liquid flow connection for carbamate solution from the LP carbamate condensation zone to the HP urea synthesis section. By avoiding the separate recycle of condensed $NH_3$, equipment costs are lower as no dedicated $NH_3$ condenser is required, moreover $NH_3$ condensation is avoided, which is considered a complex and sensitive operation, and pure $NH_3$ handling is avoided.

Preferably, a first part of the purified urea solution is used for producing melamine, and a second part of the purified urea solution is used for making one or more urea products, such as solid urea product. Preferably, both the first and second part are subjected to evaporation to form a urea melt in a (vacuum) evaporation section comprised in the urea production section. Preferably, a first part of the urea melt is supplied to the melamine production section, and preferably a second part of the urea melt is supplied to, for example, a finishing section, such as a prilling tower or granulator. Preferably, said first part used for producing melamine is at least 10 wt. %, or at least 20 wt. % or at least 30 wt. % and/or up to 50 wt. % of the total urea production. Optionally, a third part of the purified urea solution is used for preparing a liquid urea product.

The invention also provides a coupled plant for the production of urea and melamine. All preferences and details for equipment disclosed in connection with the process, apply also for the plant. The inventive process is moreover preferably carried out in a plant according to the inventing. The plant comprises a urea production section comprising a high pressure urea synthesis section (1) and a recovery section. The high pressure urea synthesis section (1) for producing urea, comprises a high pressure (HP) $CO_2$ stripper (2). The HP stripper has an outlet for a stripped urea solution (3), and an inlet for a first part (4) of a gaseous $CO_2$ feed stream used as stripping agent. The HP urea synthesis section also comprises a reaction zone and a condensation zone, as described hereinbefore. The plant comprises a melamine production section (5) having an outlet for melamine (6) product and a separate outlet for melamine off-gas (7), either as gas or as condensate. Preferences for the melamine production section (5) as discussed for the process also apply for the plant, in particular high pressure and low pressure melamine synthesis sections can be used. The melamine production section may comprise, for example, a high pressure (>70 bara) melamine synthesis reactor, a melamine melt processing section (comprising for instance a quenching unit), a crystallization unit for crystallization of melamine crystals, a mother liquor treatment section, and an off-gas washing section with, for example, water washing or urea washing.

The plant comprises a fluid flow connection, e.g. gas flow connection or liquid flow connection, or a combination thereof, for supplying said melamine off-gas (7), optionally as condensate, directly or indirectly, to the high pressure urea synthesis section (1). The plant optionally comprises a condenser for the off-gas. The condenser for off-gas can be a dedicated condensation unit or a unit for combined condensation of the melamine off-gas with other gaseous streams. The condenser is for example comprised in the urea production section, for instance in a recovery section. The fluid flow connection may comprise, e.g., a gas flow connection, or a combination of a gas flow connection, condensation unit, and a liquid flow connection.

The plant comprises a liquid flow connection for supplying the stripped urea solution (3) directly or indirectly, as a liquid, to a low pressure (LP) dissociator (8). This dissociator, e.g. heat exchanger, has an outlet for a purified urea solution (9) and an outlet for a low pressure gas stream (10). The plant comprises a low pressure (LP) carbamate condensation zone (11) configured for subjecting the low pressure gas stream to condensation with a second part of the gaseous $CO_2$ feed stream to form a carbamate solution (12). The plant comprises a gas flow line for the low pressure gas stream (10) from the low pressure (LP) dissociator (8) to the LP carbamate condensation zone (11).

The plant comprises a gas flow connection (13), e.g. a gas flow line, from a $CO_2$ supply unit (14) directly or indirectly to the LP carbamate condensation zone (11); this gas flow connection may pass through, for instance, a gas/liquid contacting unit, from a gas inlet to a gas outlet of such unit. The $CO_2$ supply unit is typically a $CO_2$ supply line at battery limit. In an example embodiment of the plant, the $CO_2$ originates from a synthesis gas plant, i.e. a plant for producing hydrogen for an upstream coupled ammonia plant which produces $NH_3$ feed for the urea plant and which also comprises a $CO_2$ yielding unit, said unit being connected to the LP carbamate condensation section. For example, the plant comprises a gas flow connection for $CO_2$ from a $CO_2$ removal unit (in particular, desorber) of a synthesis gas plant to said LP carbamate condensation zone (11). However, other sources of $CO_2$ are also possible, such as from a waste incinerator, or generally from a flue gas stream.

In some embodiments, the gas flow connection (13) is from a $CO_2$ removal unit, directly or indirectly to said LP carbamate condensation zone (11). The $CO_2$ removal unit is for instance a unit comprising an absorption unit and a desorption unit, for removing $CO_2$ from a gaseous stream using a solvent, and for releasing a $CO_2$ stream from the desorption unit into said gas flow connection.

In some embodiments, the gas flow connection (13) is from a hydrogen removal unit, said unit being configured for removing hydrogen by catalytic combustion from a $CO_2$ gas stream, to said LP carbamate condensation zone (11). The unit, also known as hydrogen convertor, uses e.g. air added to the $CO_2$ stream.

In some embodiments, the gas flow connection (13) is from a $CO_2$ compressor, in particular an intermediate stage of said compressor, to said LP carbamate condensation zone (11).

Hence, in some embodiments, the $CO_2$ supply unit (14) is the compressor, the hydrogen convertor, or a $CO_2$ removal unit of a synthesis gas plant. Accordingly, the $CO_2$ supply unit (14) may have an inlet for $CO_2$. In some embodiments, the gas flow connection (13) is provided from the $CO_2$ removal unit of a synthesis gas plant, through the compressor and hydrogen convertor, to the LP carbamate condensation zone (11).

Preferably, the plant comprises a contacting unit (15), preferably a LP stripper, for contacting the purified urea solution (9) with said second part (13) of the gaseous $CO_2$ feed stream, having a first outlet for a liquid stream and a second outlet for a gaseous stream, wherein the second outlet is connected to the LP carbamate condensation zone (11). The unit also has a gas inlet for said second part (13) of the gaseous $CO_2$ feed stream and a liquid inlet for the purified urea solution (9). The unit is preferably configured for counter-current contact, with the gas inlet at the bottom for the second part (13) of the gaseous $CO_2$ feed stream, the gas outlet at the top, the liquid inlet for the purified urea solution (9) at the top, and the liquid outlet at the bottom, and for instance with a packed or structured bed, thereby providing an LP stripper, in particular configured for adiabatic stripping at low pressure.

In a preferred embodiment, the LP carbamate condensation zone (11) is, at least in part, provided as a first compartment in indirect heat exchange with a second compartment for urea solution to be heated. Preferably the plant comprises a liquid flow line for urea solution from said LP dissociator (8) to said second compartment. Preferably said first and second compartment are provided as a shell-and-tube heat exchanger. Preferably, the second compartment is provided by the tube bundle, i.e. the tubes, and the first compartment by the shell side space. Preferably, the first compartment operates as the pre-evaporator. Preferably, the plant comprises a gas/liquid separator downstream of the outlets of the tubes to separate water vapor from the urea solution.

A gas flow connection, as used herein, indicates a flow connection for a continuously gaseous fluid. A gas flow connection may pass through units, such as a gas/liquid contacting unit, from a gas inlet to a gas outlet of the unit. A liquid flow connection, as used herein, indicates a indicates a flow connection for a continuously liquid fluid. A unit provides a liquid flow connection from a liquid inlet to a liquid outlet. For instance a decomposer and condenser, connected by a gas flow connection from decomposer to condenser, do not provide a liquid flow connection from liquid inlet of the decomposer to the liquid outlet of the condenser. However, a condense provides a liquid flow connection from a liquid inlet to a liquid outlet of a unit.

The term 'carbamate', as used herein, refers to ammonium carbamate, as that term is used in the field of urea production. In aqueous carbamate streams, the component can be present as carbonate species. Amounts of $NH_3$ and $CO_2$ for aqueous streams include the amounts present as carbonate species.

As used herein, for process streams of the urea plant (i.e. not for steam lines and not for melamine plants), high pressure (HP) is above 100 bara, for instance 120 to 300 bara, for example 140 to 200 bara. Medium pressure (MP) is for example 10 to 80 bara (including intermediate pressure of 30 to 70 bara), in particular 15 to 30 bara, and low pressure (LP) is for example 0 to 10 bara, in particular at least 1 bara, preferably at least 2 bara, or a least 4 bara; and generally up to 10 bara or preferably up to 8 bara. For instance, LP is in the range 1 to 8 bara, or 2 to 10 bara, or 3 to 10 bara, or 4 to 10 bara, or 2 to 5 bara. All pressures are bar absolute (bara).

The terms 'typical', 'suitable' and 'in particular' and derived forms are used to indicate features that can be used in some embodiments but that are not mandatory. Also preferred features are not mandatory.

The term 'melamine off-gas' as used herein indicates off-gas from the melamine production section and refers to a gas stream mainly containing $NH_3$, $CO_2$, and possibly $H_2O$.

The term 'first' as used herein for a unit or step permits the presence of further, upstream, instances of such unit or step.

As used herein, the stripping efficiency $\alpha=(2*\text{wt. \% urea}/60)/((2*\text{wt. \% urea}/60)+(\text{wt. \% NH}_3/17))$, measured at the liquid outlet of the stripper, wherein wt. % $NH_3$ includes all ammonia species including ammonium carbamate.

N/C ratio indicates the molar ratio of $NH_3$ to $CO_2$, for gas streams on the basis of $NH_3$ and $CO_2$; for carbamate solutions on the basis of $NH_3$, $CO_2$ and carbamate, and for a synthesis section based on the theoretical initial reaction mixture consisting of $H_2O$, $NH_3$ and $CO_2$. The N/C ratio for carbamate condenser refers to the N/C ratio at the liquid outlet. The free N/C ratio for urea solutions is calculated on the basis of $NH_3$, $CO_2$ and carbamate, excluding urea.

Indirect heat exchange, as used herein, refers to heat exchange through a heat-exchanging wall, in the context of the invention through a heat exchanging wall that is in contact with urea solution to be heated at a first side and with gas comprising $CO_2$ and $NH_3$, which gas is condensing to form carbamate solution, on a second side of said wall.

Aspects of the invention are now illustrated by the following example(s) which do not limit the invention or the claims.

EXAMPLE 1

A urea plant is considered and simulated with 30 wt. % of the urea melt supplied to the melamine production section and with the corresponding amount of melamine off-gas recycled to the urea synthesis section. Ton is metric ton and values are approximate.

The general design of the plant is as in FIG. 1; with MP adiabatic flash of the urea solution between the HP stripper and the LP dissociator.

Case 1: The amount $CO_2$ feed to the HP $CO_2$ stripper is 86 ton/hour, used for HP stripping, the $CO_2$ feed to the LP section, in particular to the LP stripper, is 10 ton/hr. The LP carbamate condensation section comprises two condensation units in series. The first LP carbamate condenser receives gas from the LP dissociator and an LP $CO_2$ feed stream; and is provided as the shell-side of a pre-evaporator for urea solution, with urea solution to be heated in the tubes. The second LP carbamate condenser receives gas and liquid from the first LP carbamate condenser and is operated with cooling water or circulating cooling water.

At optimum operation, the first LP condensation unit is operated with a liquid outlet temperature of 93° C., liquid outlet temperature of the second LP condensation unit is 66° C., at about 5.4 bara. The urea solution at the outlet of the HP stripper has an N/C ratio of 2.8 (free N/C, i.e. on the basis of $NH_3$, $CO_2$ and carbamate, excluding urea). The N/C ratio of the carbamate solution at the liquid outlet of the second LP condensation unit is 2.77. This carbamate solution is supplied to an MP carbamate condenser having liquid outlet N/C ratio of 2.35 from where it is recycled to the HP urea synthesis section. The MP carbamate condense also received gas from the MP flash.

Case 2, which is less preferred: The amount of $CO_2$ feed to the LP section is reduced to 3 ton/hour; the amount $CO_2$ feed to the HP section is 93 ton/hour. At optimum operation, the first LP condensation unit is operated with a liquid outlet temperature of 91° C., liquid outlet temperature of the second LP condensation unit is 57° C., at about 5.4 bara. The urea solution at the outlet of the HP stripper has an N/C ratio of 2.7 (free N/C). The N/C ratio of the carbamate solution at the liquid outlet of the second LP condensation unit is 3.2. This carbamate solution is supplied to an MP carbamate condenser having liquid outlet N/C ratio of 2.55 from where it is recycled to the HP urea synthesis section.

In case 2, the surface area of the LP carbamate condensers must be larger and the duty of the WWT increases. Furthermore, the reflux condenser temperature decreases from 68° C. in case 1 to 50° C. in case 2; requiring a larger reflux condenser in the WWT. The decrease in overall steam consumption at the HP stripper due to the increased flow of $CO_2$ feed is only marginal. Hence, the performance of the coupled plant and process is better in Case 1 than in Case 2. The WWT load is higher in Case 2 by reason of higher N/C ratio in the MP and LP, which leads to a higher load of absorbers for uncondensed gas from the respective condensers, with aqueous liquid from the absorbers being treated in the WWT section.

Case 3 (comparative): The amount of $CO_2$ feed to the LP section is reduced to 0 ton/hour; the amount $CO_2$ feed to the HP section is 96 ton/hour. The aim is 30% melamine integration, and keeping MP flash. Simulations show that a separate $NH_3$ condenser is necessary in the recovery section in Case 3, with separate recycle of condensed $NH_3$, otherwise there are large ammonia losses to the atmosphere in Case 3.

EXAMPLE 2

Case 1A: Case 1A is the same as in Case 1, with the following additional details. In the first LP carbamate condenser, a total vapor feed as 78 ton/h is supplied (65 ton/h of this vapor originates from LP rectification/dissociation, 13 ton/h from LP $CO_2$ stripping). About 57 ton/h aqueous carbamate is added to first carbamate condenser, provided as approx. 33 tons/h originating from a reflux condenser and 24 ton/h originates from the atmospheric condenser. The average water concentration of added aqueous carbamate is approx. 50 wt. %. From the single outlet of the first condenser outlet to inlet of the second condenser, the stream is provide by about 105 ton/h liquid at about 95° C. (N/C approx. 2.4), and about 30 ton/h vapor at about 95° C. At the outlet of the second condenser, total liquid is about 132 tons/h at about 69° C. (N/C approx. 2.8); and the non-condensed gas is about 3 ton/h at about 69° C. This vapor is supplied to an atmospheric condenser.

The invention claimed is:

1. A coupled process for the production of urea and melamine, the process comprising:
   producing urea in a high pressure urea synthesis section comprising a high pressure (HP) $CO_2$ stripper yielding a stripped urea solution, wherein the HP $CO_2$ stripper uses a first part of a gaseous $CO_2$ feed stream as stripping agent;
   producing melamine in a melamine production section thereby also releasing melamine off-gas;
   supplying said melamine off-gas, optionally as condensate, directly or indirectly to the high pressure urea synthesis section;
   supplying the stripped urea solution directly or indirectly via a liquid flow connection to a low pressure (LP) dissociator, yielding purified urea solution and a low pressure gas stream;
   subjecting the low pressure gas stream to condensation in a low pressure (LP) carbamate condensation zone with a second part of the gaseous $CO_2$ feed stream to form a carbamate solution.

2. A process according to claim 1, wherein said purified urea solution is brought in counter-current contact in a contacting unit with said second part of the gaseous $CO_2$ feed stream, yielding a liquid stream and a gaseous stream, and the gaseous stream is supplied to the LP carbamate condensation zone.

3. A process according to claim 2, wherein said second part of the gaseous $CO_2$ feed stream is used for low pressure stripping of the purified urea solution.

4. A process according to claim 1, wherein the melamine off-gas is condensed into a first carbamate stream which is supplied, directly or indirectly, to a urea reaction zone, wherein preferably a) the first carbamate stream is supplied to the high pressure urea synthesis section, or b) the melamine off-gas is supplied as a gaseous stream to the high pressure urea synthesis section and is condensed into the first carbamate stream in a carbamate condenser comprised in said high pressure urea synthesis section.

5. A process according to claim 1, wherein said condensation in said LP carbamate condensation zone is, at least in part, conducted in indirect heat exchange with a urea solution to be heated.

6. A process according to claim 1, comprising a medium pressure treatment of the stripped urea solution upstream of the LP dissociator.

7. A process according to claim 6, wherein the medium pressure treatment comprises adiabatic flashing or consists of adiabatic flashing.

8. A process according to claim 6, wherein said medium pressure treatment comprises heating of the stripped urea solution.

9. A process according to claim 1, wherein the second part of the gaseous $CO_2$ feed stream is 2-20 mol % of the total $CO_2$ feed stream.

10. A process according to claim 1, wherein the amount of $CO_2$ in the melamine off-gas stream supplied to the HP urea synthesis section, in kg/hr, is at least 5% of the amount, in kg/hr, of $CO_2$ converted into urea in the HP urea synthesis section, preferably at least 10% of said amount.

11. A process according to claim 1, wherein the purified urea solution, optionally after being brought in counter-current contact with said second part of the gaseous $CO_2$ feed stream, is expanded to atmospheric pressure with the formation of a gas stream, wherein said gas stream is condensed at atmospheric pressure.

12. A process according to claim 1, wherein the LP carbamate condensation zone is operated with a pressure of at least 3.0 bara, and wherein the LP carbamate condensation zone receives the second part of the gaseous $CO_2$ feed stream as a gas stream at a pressure of at least 3.0 bara.

13. A process according to claim 1, wherein LP is at least at least 2 bara, preferably at least 4 bara.

14. A process according to claim 1, wherein the second part of the gaseous $CO_2$ feed stream is at least 5 mol. % and less than 25 mol. % of the total $CO_2$ feed stream on the basis of $CO_2$; and wherein preferably the amount of $CO_2$ in the gas stream at a gas outlet of said contacting unit is at least 5 mol. %.

15. A coupled plant for the production of urea and melamine, the plant comprising:
- a high pressure urea synthesis section for producing urea, comprising a high pressure (HP) $CO_2$ stripper having an outlet for a stripped urea solution, and an inlet for a first part of a gaseous $CO_2$ feed stream used as stripping agent;
- a melamine production section having an outlet for melamine and an outlet for melamine off-gas;
- a fluid flow connection for supplying said melamine off-gas, optionally as condensate, directly or indirectly to the high pressure urea synthesis section;
- a liquid flow connection for supplying the stripped urea solution directly or indirectly to a low pressure (LP) dissociator having an outlet for a purified urea solution and an outlet for a low pressure gas stream;
- a low pressure (LP) carbamate condensation zone configured for subjecting the low pressure gas stream to condensation with a second part of the gaseous $CO_2$ feed stream to form a carbamate solution, the plant comprising a gas flow connection from a $CO_2$ supply unit to the LP carbamate condensation zone and a gas flow line for said low pressure gas stream from said low pressure (LP) dissociator to said low pressure (LP) carbamate condensation zone.

16. A coupled plant according to claim 15, wherein the gas flow connection is from a $CO_2$ removal unit to said LP carbamate condensation zone.

17. A coupled plant according to claim 15, wherein the gas flow connection is from a hydrogen removal unit, said unit being configured for removing hydrogen by catalytic combustion from a $CO_2$ gas stream, to said LP carbamate condensation zone.

18. A coupled plant according to claim 15, wherein the gas flow connection is from a $CO_2$ compressor, in particular an intermediate stage of said compressor, to said LP carbamate condensation zone.

19. A coupled plant according to claim 15, comprising a contacting unit, preferably a LP stripper, for contacting the purified urea solution with said second part of the gaseous $CO_2$ feed stream, having a first outlet for a liquid stream and a second outlet for a gaseous stream, wherein the second outlet is connected to the LP carbamate condensation zone.

20. A coupled plant according to claim 15, wherein said LP carbamate condensation zone is, at least in part, provided as a first compartment in indirect heat exchange with a second compartment for urea solution to be heated, and wherein the plant preferably comprises a liquid flow line for urea solution from said LP dissociator to said second compartment, and wherein preferably said first and second compartment are provided as a shell-and-tube heat exchanger.

* * * * *